United States Patent [19]

Lapides

[11] 4,393,711

[45] Jul. 19, 1983

[54] APPARATUS AND METHOD FOR ULTRASONIC DETECTION OF FLAWS IN POWER PLANT PIPING SYSTEMS

[75] Inventor: Melvin E. Lapides, Mountain View, Calif.

[73] Assignee: Electric Power Research Institute, Inc., Palo Alto, Calif.

[21] Appl. No.: 206,627

[22] Filed: Nov. 13, 1980

[51] Int. Cl.³ ............................................. G01N 29/04
[52] U.S. Cl. ...................................... 73/592; 73/60 L; 73/1 DV
[58] Field of Search ................. 73/592, 602, 614, 627, 73/1 DV; 364/507, 582

[56] References Cited

U.S. PATENT DOCUMENTS

| | | | |
|---|---|---|---|
| 3,453,871 | 7/1969 | Krautkramer | 73/602 |
| 3,756,071 | 9/1973 | Dury | 73/602 |
| 3,933,026 | 1/1976 | Ham et al. | 73/1 DV |
| 4,173,139 | 11/1979 | Conn | 73/1 DV |
| 4,182,154 | 1/1980 | Lather et al. | 73/1 DV |
| 4,290,308 | 9/1981 | Dau | 73/602 |

Primary Examiner—Anthony V. Ciarlante

Attorney, Agent, or Firm—Flehr, Hohbach, Test, Albritton & Herbert

[57] ABSTRACT

A method of in-service ultrasonic detection of intergranular stress corrosion cracking conditions in pipe sections of nuclear power plants. A plurality of ultrasonic return signal features and an associated general form of algorithmic combination are selected on the basis of ultrasonic pipe studies to use in distinguishing return signals from cracking conditions and geometric reflectors. A calibration pipe sample having a prearranged configuration with geometric reflectors substantially corresponding to the unknown pipe section and at least one known cracking condition is provided. Sequential ultrasonic examinations are performed using the calibration pipe sample first to enable tuning of the algorithmic combination to optimize the ability to distinguish return signals from geometric reflectors and known cracking conditions followed by an ultrasonic examination of the pipe section using the same selected return signal features and the selected algorithmic combination of the values to ascertain presence or absence of a cracking condition. A kit of parts including a crack detection instrument and a variety of calibration pipe samples corresponding to the various pipe section configurations in a nuclear power plant is also disclosed.

6 Claims, 9 Drawing Figures

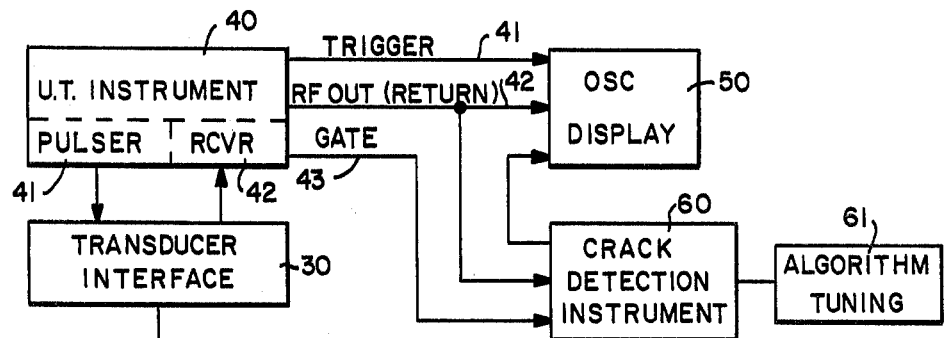
FIG.—1A
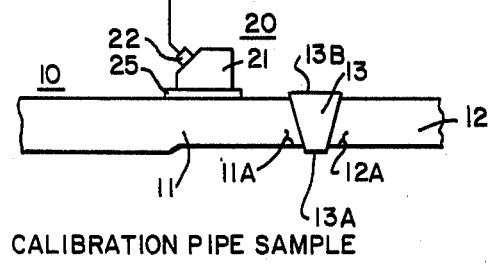
CALIBRATION PIPE SAMPLE
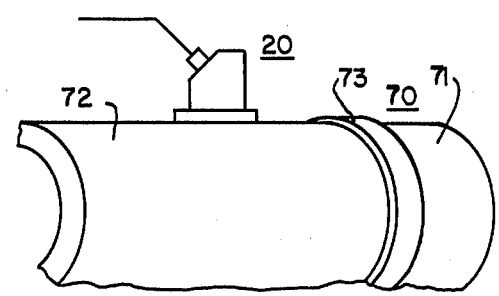
IN-SERVICE PIPE SECTION
FIG.—1B
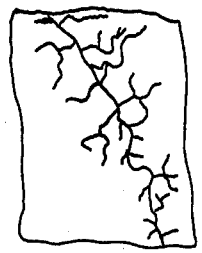
FIG.—2
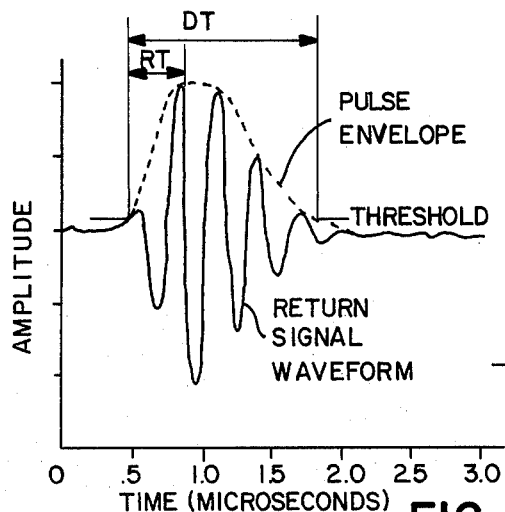
FIG.—3
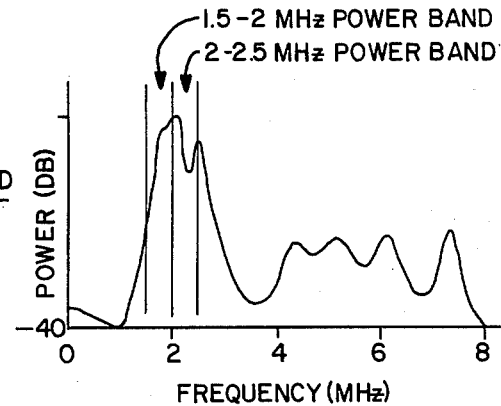
FIG.—4

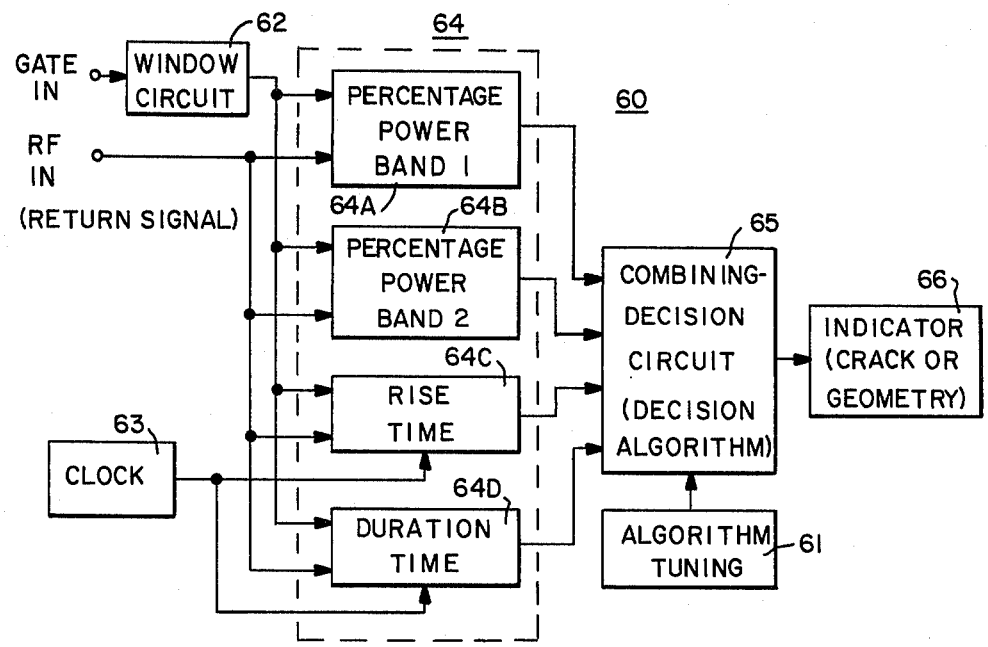
FIG.—5
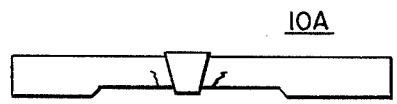
FIG.—6A
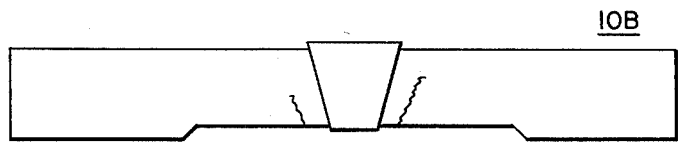
FIG.—6B
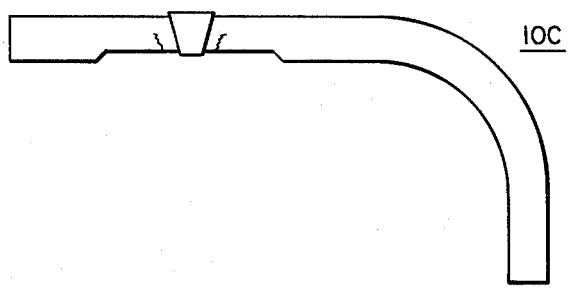
FIG.—6C

APPARATUS AND METHOD FOR ULTRASONIC DETECTION OF FLAWS IN POWER PLANT PIPING SYSTEMS

This invention relates generally to apparatus and methods for non-destructive examination (NDE) of power plant piping systems. Specifically, the invention relates to apparatus and methods for ultrasonic examination of stainless steel piping in power plants to ascertain the presence or absence of flaws therein. More specifically, the invention relates to apparatus and methods for detecting intergranular stress corrosion cracking conditions in stainless steel pipe systems which is an especially acute problem in a boiling water nuclear power plant.

Federal and State laws require that nuclear power plants be inspected both prior to being placed in service and periodically during operation of the plant. These mandated inspections are nondestructive evaluations of the nuclear power plant components. Specific procedures for the calibration, inspection routine, equipment, and requirements for recording and reporting the results of the evaluations have been established for each nuclear power plant component. Ultrasonic testing (UT) is one of the NDE techniques that is commonly required for many of the power plant components. One of the main components of every nuclear power plant is a stainless steel piping system which typically involves sections of stainless steel piping welded together to carry a liquid such as reactor coolant which is, of course, a critical aspect of every nuclear power plant.

Intergranular stress corrosion cracking (IGSCC) is a major degradation mechanism in stainless steel piping systems of boiling water nuclear power plants. IGSCC conditions in stainless steel piping systems most often occur in regions adjacent weld areas in the pipe sections and are generally thought to originate on the interior walls of the pipe near the weldment and then grow both radially and circumferentially into the pipe section due to the combined effect of stress, heat, and corrosion from the oxygenated liquid passing through the pipe. Typically, IGSCC conditions in a pipe are called "tight" cracks which visually appear as fissures or veins extending throughout a volume of the pipe.

Several of the qualities of IGSCC conditions and the stainless steel pipe medium in which they occur render the detection of the IGSCC condition difficult with conventional UT methods. The tightness of the intergranular stress corrosion cracks results in an ultrasonic return signal from the IGSCC discontinuity, which is generally small in amplitude. Furthermore, the material of typical stainless steel piping has grains which represent acoustic discontinuities which produce UT return signals of an amplitude generally comparable to return signals from IGSCC conditions. In addition, the IGSCC conditions often occur in regions of the pipe section which include a substantial number of other geometric reflectors which may produce return signals of comparable magnitudes to those of the IGSCC condition.

Consequently, detection of IGSCC conditions in stainless steel piping systems of nuclear power plants is a difficult process. Furthermore, sizing of a detected IGSCC condition in order to determine whether the condition mandates replacement of the pipe section in which it occurs is equally difficult.

Nuclear power plant inspection requirements usually mandate a conservative replacement approach because of the risks involved in leakages from power plant piping systems. Large stainless steel piping is often used in the primary reactor coolant system. If conventional UT inspection based on current standards produces an indication of a possible critical IGSCC condition, conservative replacement criteria may mandate unplanned shutdown of the reactor. Such a reactor outage may cost a utility company as much as five hundred thousand dollars per day, and a reactor shutdown for replacement of a large stainless steel pipe section may take a week to ten days, including the time required for cool down of the reactor and piping systems, removal of insulation surrounding the pipe section, replacement of the suspected pipe section and restarting of the reactor. Sometimes an after-the-fact examination of the "defective" pipe section shows that a critical IGSCC condition was not present and the power plant could have continued operating safely until a planned shutdown period.

Accordingly, it is a principal object of this invention to provide an improved method for detecting cracking conditions in a pipe section.

More specifically it is an object of this invention to provide an improved method for in-service detection of IGSCC conditions in sections of a nuclear power plant piping system.

It is a further object of this invention to provide an improved method for detecting a critical IGSCC cracking condition in a pipe section of a nuclear power plant piping system.

It is another object of this invention to provide an improved kit of apparatus for in-service ultrasonic detection of critical IGSCC cracking conditions in nuclear power plant pipe sections.

One aspect of this invention features a method of in-service detection of a cracking condition in a pipe section of predetermined configuration in which the first step of the method involves selecting a plurality of ultrasonic return signal features and an associated general form of algorithmic combination thereof whose values are useful in distinguishing return signals from a cracking condition and from geometric reflectors based on ultrasonic examination studies on a plurality of pipe samples having a variety of known geometric reflectors and known cracking conditions. Another step in the method is the providing of a calibration pipe sample having a prearranged configuration with geometric reflectors substantially corresponding to the unknown pipe section and at least one known cracking condition of the type which is desired to be detected and which has been previously studied. The next step is to perform an ultrasonic examination of the calibration pipe sample in terms of the selected return signal features to select a specific form of said algorithmic combination of the values thereof to optimize distinguishing of return signals from the geometric reflectors in the calibration pipe sample and the known cracking condition therein. The final step is then to perform an ultrasonic examination of the pipe section of unknown condition using the same selected return signal features and the selected algorithmic combination of the values thereof to ascertain the presence or absence of a cracking condition therein. Where the pipe test section and the pipe samples used in the method are stainless steel pipe sections subject to intergranular stress corrosion cracking, the known cracking condition provided in the calibration pipe sample is an intergranular stress corrosion cracking condition and preferably the selected return signal features include selected frequency spectrum and waveform features.

Where the above-described method is to be utilized to perform decision sizing of the cracking condition, the calibration pipe sample is provided with a known cracking condition having a critical size and the algorithmic combination of the selected return signal features is selected to enable distinguishing cracking conditions of critical size from cracking conditions of subcritical size.

Another aspect of this invention features a kit of apparatus used for in-service ultrasonic detection of cracking conditions in pipe sections of different varieties and configurations in conjunction with an ultrasonic test instrument and a transducer assembly. The kit includes a plurality of different calibration pipe samples each having a prearranged configuration with inherent geometric reflectors substantially corresponding to those of one of the pipe sections and a known cracking condition. The kit further includes a crack detection instrument adapted to receive output signals from the ultrasonic test instrument representing return signal waveform information from a selected pipe section under test for indicating whether the return signal is from a geometric reflector or from a cracking condition therein. The crack detection instrument comprises means for measuring the values of a plurality of preselected features of the return signal waveform information, means for combining the measured feature values in accordance with a decision algorithm, and means for registering when the algorithmically combined feature values indicate a return signal from a cracking condition. The combining means include algorithm tuning means adapted to be adjusted while the detection instrument is receiving return signal waveform information from a preselected one of the calibration pipe samples corresponding to the selected pipe section to tune the decision algorithm to optimize the sensitivity and specificity of the instrument for the detection of the cracking condition.

In some embodiments where the kit is to be used for critical sizing of the cracking condition, the known cracking conditions in the calibration pipe samples are critical flaws and the aglorithm tuning means is adapted to be adjusted while the detection instrument is receiving return signals from a critical flaw on a preselected calibration pipe sample such that the registering means will indicate a return signal from a cracking condition of magnitude equal to or greater than the critical flaw when the detection instrument is used on a selected pipe section under test.

The method of this invention provides an enhanced ability to detect cracking conditions in pipe sections which are difficult to detect with accuracy using conventional, manual UT methods. The method can be carried out utilizing special purpose analog/digital signal processing circuitry or straightforward digital signal processing. The use of a calibration pipe sample for tuning the algorithmic combination of the values of selected return signal features provides not only a check on the working condition of the instrumentation utilized to carry out the method, but enables the optimization of the decision algorithm and the variation thereof for different pipe sample configurations.

The aspect of this invention which involves a kit has the advantage of providing the operator of the testing equipment with the assurance that the instrumentation is capable of detecting cracking conditions in pipe sections corresponding to those being tested, and may eliminate to a large extent the subjectivity involved in conventional manual UT investigations.

Where the method and apparatus of this invention are utilized for decision sizing of cracking conditions, a more objective and certain basis to judge whether or not a power plant must be shut down to replace a pipe section with a critical flaw therein may be provided. Other objects, features, and advantages of this invention will be apparent from a consideration of the following detailed description taken in conjunction with the accompanying drawings.

FIGS. 1A and 1B are block-schematic drawings of an ultrasonic test system including apparatus in accordance with this invention and apparatus for carrying out the method of this invention.

FIG. 2 is a representation of a intergranular stress corrosion cracking condition in a pipe section.

FIG. 3 is a graph of an ultrasonic return signal waveform useful in explaining the method of this invention.

FIG. 4 is a graph of the power versus frequency spectrum of an ultrasonic return signal useful in explaining the method of this invention.

FIG. 5 is a block schematic diagram of a crack detection instrument useful in the method of this invention and forming a part of the apparatus of this invention.

FIGS. 6A, 6B, and 6C illustrate various parts of a kit which constitutes one aspect of this invention.

The apparatus depicted in FIGS. 1A and 1B illustrates an ultrasonic testing (UT) setup in accordance with this invention. The apparatus depicted is capable of carrying out the basic method involved in this invention and includes some of the parts of the kit according to this invention. Some portions of the equipment depicted in FIG. 1A are conventional apparatus utilized in conventional manual UT investigations. These conventional items are a transducer assembly 20, a transducer interface circuit 30, a UT instrument 40, and an oscilloscope display 50. Transducer assembly 20 includes a coupling block 21 and transducer 22. A viscous liquid couplant 25 is provided for low impedance coupling into the body of the item being tested. The UT instrument 40 conventionally includes a pulser 41 and receiver 42. As background for an explanation of this invention, it will be helpful to consider first the general approach to a conventional manual UT investigation. A conventional manual UT investigation starts with a calibration of the instrumentation utilizing a calibration block with a flaw of substantial size in the form of a notch or hole formed in the block to serve as a sample flaw. Utilizing the transducer assembly 20 in conjunction with the UT instrument 40 and the oscilloscope display 50 the equipment is calibrated by analyzing the return signals from the calibration block to construct a distance amplitude correction (DAC) curve. Generally this is done by placing the transducer assembly 20 in a position on the calibration block whereas maximum response from the calibration flaw is produced. The gain of the instrument is then adjusted to bring the primary reference response to about 75% of the full screen height of the CRT screen and the amplitude of the signal is marked on the screen with grease pencil or something similar. Then the transducer assembly is positioned on the calibration block to obtain the maximum response from the other nodal positions and each time the amplitude of the maximum response is marked on the oscilloscope screen. When the sequence of response points at various nodal positions has been marked, these marks are joined by a smooth curved line which then represents the DAC curve. Then using the same gain settings the transducer assembly is positioned on the pipe section and the return signals from the pipe section are examined on the CRT screen as the transducer is positioned in various places on the pipe section under test. Based on a reference standard those return signals which have amplitude a certain percentage of the reference DAC amplitude are typically recorded. Based on the recorded data from various positions, a judgment is made as to the existence of a flaw in the pipe section.

As previously explained, this conventional, manual UT examination method is very difficult to perform with reliability in detecting IGSCC conditions in stainless steel pipe sections. Therefore, according to this invention, a crack detection instrument 60 is provided for analyzing the output signals from the UT instrument 40 to provide a more sophisticated analysis of the return signal information to assist in determining whether a return signal corresponds to a cracking condition in the pipe section under study. The crack detection instrument 60 may take various forms for carrying out the general method steps of this invention. Before discussing the details of the method of this invention, it will be helpful to understand the general approach to be utilized in connection with the crack detection instrument 60 provided in accordance with this invention.

One of the basic features of crack detection instrument 60 is the implementation of a return signal waveform analysis based on a preselection of certain return signal features whose values are combined in accordance with a decision algorithm to produce an indication of whether the return signal corresponds to a cracking condition or some geometric reflector within the pipe section under test. The general principle of this invention is to utilize a calibration pipe sample 10 in FIG. 1A which has a prearranged configuration with known geometric reflectors substantially corresponding to the unknown pipe section under test and also has at least one known cracking condition therein. Thus for example the calibration pipe sample 10 shown in FIG. 1A consists of a pair of pipe segments 11 and 12 joined together by a weld 13 with reference cracking conditions 11A and 12A provided in the inside wall of the pipe section near the root 13A of weld 13. As will later be discussed the known cracking conditions 11A and 12A may either be critical or subcritical cracking conditions depending on whether the crack detection instrument 60 is to be used for initial crack detection and monitoring or for decision sizing based on some preset standard of critical flaw size. Critical flaw size may involve parameters such as crack depth, percentage crack depth, crack length, etc.

The concept of this invention is to utilize the calibration pipe sample with the reference cracking conditions therein both as a checking mechanism for the integrity of the operation of the crack detection instrument 60 and as a way of tuning the algorithm in the crack detection instrument 60 for the particular parameters of the calibration pipe sample to optimize the sensitivity of the instrument to the reference cracking condition. Consequently, the transducer assembly 20 is placed on the calibration pipe sample such that the ultrasonic beam is directed into the cracking condition contained therein. Algorithm tuning controls 61 are then manipulated to tune the decision algorithm in crack detection instrument 60 such that the crack detection instrument 60 will register the presence of a cracking condition when the beam is intercepting the cracking condition 11A in calibration pipe sample 10 but will not register cracking condition when the beam is directed to a section of the calibration pipe sample containing only geometric reflectors. In another mode of operation involving decision sizing, the algorithm tuning function may be carried out while the beam is directed to a section of the calibration pipe sample containing a critical cracking condition. In this way the algorithm in the crack detection instrument 60 may be tuned to respond with a positive indication only when the selected return signal features are representative of a cracking condition equal to or exceeding that of the reference critical cracking condition and will not indicate a positive output when the return signal corresponds to a geometric reflector or to a subcritical cracking condition. By providing both critical and subcritical cracking conditions in the same calibration pipe sample (or in two similar samples), algorithm tuning may be carried out by alternately directing the ultrasonic beam to the critical and the subcritical cracking condition for checking the tuning of the algorithm to respond to one and not the other. After the algorithm tuning operation has been performed using the calibration pipe sample, the transducer assembly is then transferred to the in-service pipe section to be tested, and the return signals from the UT instrument are analyzed by the crack detection instrument in accordance with the tuned algorithm to indicate the presence or absence of a cracking condition in the various portions of the in-service pipe section that are analyzed.

The first step of the method of in-service ultrasonic detection in accordance with this invention involves selecting a plurality of ultrasonic return signal features and an associated general form of algorithmic combination thereof whose values are useful in distinguishing return signals from cracking conditions and from geometric reflectors. This selection process is generally best carried out by performing extensive ultrasonic examination studies of a plurality of pipe samples having a variety of known geometric reflectors and known cracking conditions. These ultrasonic examination studies may be carried out by digitizing return signal information utilizing a high speed analog to digital converter and storing the digitized signal information in a digital data storage apparatus such as a magnetic disk for use in a computer analysis to develop the decision algorithm. By conducting a statistically significant number of evaluations of return signals from various known geometric reflectors and cracking conditions, it is possible to analyze the stored data to determine a plurality of return signal features whose values can be used in distinguishing return signals from geometric reflectors from those of known cracking conditions. One specific approach to conducting these ultrasonic examination studies and selecting ultrasonic return signal features is set forth in Technical Report R79-EPRI-1 entitled, "Manual Analog Call Confirmer Design, Development, and Test", dated September 1979, which is available from the Electric Power Research Institute, Inc., Palo Alto, California. The material in this report relating to the selection of ultrasonic return signal features for distinguishing return signals from cracking conditions and from geometric reflectors is hereby specifically incorporated by reference.

FIGS. 3 and 4 illustrate four examples of return signal features which may be used in distinguishing return signals from cracking conditions and geometric reflectors. FIG. 3 shows a typical return signal waveform plotted in terms of signal amplitude versus time. For purposes of illustration, the pulse envelope of the return signal is indicated by the dashed curve on FIG. 3. As discussed in the above-mentioned technical report, two of the return signal features which have been identified to be of value in distinguishing cracking conditions and geometric reflectors are the pulse envelope rise time (RT) and the pulse envelope duration time (DT) which are labeled on FIG. 3.

FIG. 4 depicts a graph of the return signal frequency spectrum showing the power level in the return signal at various frequencies. As set forth in the above-referenced technical report, two return signal features which are useful in distinguishing signals from cracking conditions and from geometric reflectors are the percentage of return signal power in a pair of adjacent power bands of the frequency spectrum each having a width of 0.5 megahertz with the first power band extending between 1.5 and 2 megahertz and the other between 2 and 2.5 megahertz. These power bands are selected in connection with an ultrasonic test instrument which utilizes a 1.5 megahertz transducer producing signals occupying a band width of 0.5 to 2.5 megahertz. It should, of course, be understood that the selection of the 0.5 megahertz power bands will depend on the operating frequency of the ultrasonic transducer so that one of the aspects of algorithm tuning in accordance with this method may involve the tuning of the power bands for a particular ultrasonic transducer assembly to optimize the decision algorithm with respect to that transducer.

It has generally been found that the aforementioned four return signal features provide the basis for constructing a decision algorithm utilizing appropriately weighted combinations of the values of these return signal features. One of the standard ways of combining the values of these return signal features into a decision algorithm is the use of a Fisher Linear Discriminant approach which involves summing weighted combinations of the return signal feature values to form a test statistic signal. This test statistic signal may then be compared logically with a certain preselected threshold value as a basis for deciding whether a return signal corresponds to a cracking condition or a geometric reflector. One approach to implementing such a Fisher Linear Discriminant function and a decision threshold condition is set forth in a co-pending patent application in the name of A. E. Zeger et al., entitled "System and Method for Measuring Ultrasonic Return Signals", Ser. No. 206,626, filed Nov. 13, 1980. This approach is also set forth in the above-referenced technical report.

It should be understood that while an exemplary approach to implementing the method of this invention involves a selection of the above-referenced four return signal features, the method of this invention is not limited to the selection of any particular number or type of return signal features. The process of selecting the number of return signal features to be used in the particular features to be selected depends on the target cost of the instrumentation to be utilized in implementing the method. Since the main purpose of this invention is to provide a relatively inexpensive crack detection instrument which can be readily utilized in the field to assist in detecting IGSCC conditions, the above indicated four return signal features were selected in order to provide a crack detection instrument with sufficient reliability at reasonable cost.

The next step of the method of this invention is to provide a calibration pipe sample having a prearranged configuration with geometric reflectors substantially corresponding to the unknown pipe section to be tested and having at least one known cracking condition. A variety of approaches can be taken to implementing this step of the method. For example, calibration pipe samples may be obtained by utilizing sections of pipe which have been taken from actual in-service nuclear power plant pipes which have been removed and which have ascertained cracking conditions. Another approach is to produce a calibration pipe sample by artificially inducing the growth of a cracking condition in a pipe sample. Two techniques for artificially inducing IGSCC conditions in a stainless steel pipe are reported in EPRI Report NP-1234-SR entitled "Non-Destructive Evaluation Program: Progress in 1979", dated December 1979, available from Electric Power Research Institute of Palo Alto, California. The two reports relating to these two methods are sections of the above-identified report entitled "Quick Reaction Capability for Manufacture of Flawed Specimens", RP-1448-6 at page 31-1 of the report and "Production of Controlled Intergranular Stress Corrosion Cracking of Large Pipes", RP-1448-7 on page 32-1 of the above-identified report.

FIG. 2 illustrates a sectional microstructure of a typical "tight" IGSCC condition generated by one of the techniques reported. Using these artifical crack generation techniques, it is thus possible to provide a plurality of calibration pipe samples where each pipe sample corresponds in geometric configuration to one of the types of pipe sections which must be analyzed in a typical boiling water type of nuclear power plant installation. Accordingly, the calibration pipe samples provided may have generally the same pipe wall thickness and the same weld characteristics and the same types of geometric reflectors. Generally the calibration pipe samples will be formed of the same stainless steel material as the in-service pipe sections to be tested and will thus have the same tendency to produce return signals from grains in the stainless steel piping material as well as other geometric reflectors.

The next step of the method according to this invention is to perform an ultrasonic examination of the calibration pipe sample 10 in FIG. 1A in terms of the selected return signal features (i.e. those identified in FIGS. 3 and 4) to select a specific form of the selected algorithmic combination of the values thereof to optimize the distinguishing of return signals from geometric reflectors and from the known cracking condition in the calibration pipe sample. Stated another way, this step involves tuning the algorithm involved in crack detection instrument 60 in terms of the geometric parameters of the calibration pipe sample in order to optimize the decision algorithm and thereby to optimize the sensitivity and specificity of the instrument for detection of the cracking condition. The approach to performing this step depends, of course, on the type of instrumentation which is employed as the crack detection instrument. The exemplary crack detection instrument which is disclosed in the above-referenced co-pending Abrams application involves an analog measurement of the percentage signal power in two preselected frequency bands of the return signal frequency spectrum and a digital measurement of the rise time and duration time of the detected pulse envelope depicted schematically in FIG. 3. The rise time and duration time digital measurements are converted to analog signal values and the combining circuit performs a weighted summing of the analog signal values corresponding to the preselected signal features in accordance with a Fisher Linear Discriminant function and applies the resulting analog signal to a decision circuit which compares the test statistic signal with a reference voltage to indicate whether the crack threshold of the test statistic signal has been exceeded. Within the combining-decision circuit, potentiometers are provided for selecting the weighting factors involved in the Fisher Linear Discriminant combination of input signal feature values and a potentiometer setting for the comparison voltage in the decision circuit are also provided. Accordingly, one way of algorithm tuning is to manipulate the weighting and decision threshold potentiometers to optimize the response of the crack detection instrument to the cracking condition in the calibration pipe sample. It should be understood, however, that this tuning of the algorithm will generally be done in a controlled fashion. Generally the process of tuning the decision algorithm will involve a limited manipulation of the weighting factors in the combining circuit within a relatively narrow range since it is anticipated that for each calibration pipe sample a specific tuning protocol will be established for setting the initial decision algorithm with fine tuning thereof based on applying the transducer assembly to the calibration pipe sample to manipulate the tuning controls in an orderly progression.

The use of the algorithm tuning step based on return signals from a calibration pipe sample is expected to enable the operator of the crack detection instrument to optimize the decision algorithm for the particular transducer, couplant material, pipe wall thickness and pulser-receiver characteristic involved in the apparatus being used. Thus the performance of this step in the method of this invention enables not only a check by the operator on the condition of the operation of the various instruments but an optimization procedure which enhances the reliability of detecting actual cracking conditions in the in-service pipe section to be examined in performance of the last step in the process of this invention.

The last step in the basic process of this invention involves performing an ultrasonic examination of the test pipe section using the same selected return signal features and the selected algorithmic combination of the values thereof to ascertain the presence or absence of a cracking condition in the test pipe section. Having done the decision algorithm tuning, the performance of this step of the method involves a straightforward adaptation of the conventional manual UT examination with the crack detection instrument 60 either assisting in the decision as to the existence of a crack or being the primary decision arbiter as to the existence of such a crack.

At this point it should be appreciated that the method of this invention is applicable to two modes of ultrasonic examination. The first mode is simply crack detection and the second mode is decision sizing of a cracking condition. In the first mode, the calibration pipe sample will be provided with a calibration flaw which generally will be the minimum flaw which is capable of being detected by the crack detection instrument. This mode may be employed for initial detection of possible cracking conditions in certain critical areas of the piping system of a boiling water nuclear reactor. Such initial detection may be followed up by periodic monitoring of the growth rate of a suspected cracking condition to determine whether the cracking condition is growing and the rate at which propagation of the condition is occurring. The second mode of performing the method involves decision sizing wherein the method is devoted to detecting the presence of a critical cracking condition or critical flaw size in the test pipe section under examination. Decision sizing utilizing the method of this invention involves performing the algorithm tuning or selection step of the method using a calibration pipe sample which contains a critical cracking condition. Under certain circumstances it may be desirable for the calibration pipe sample to contain both subcritical and critical flaws so that the tuning of the decision algorithm to distinguish critical and subcritical cracking conditions can be checked utilizing the calibration pipe sample. In some instances it may be possible to produce the critical and subcritical cracking conditions in the same calibration pipe sample and in other instances it may be necessary to utilize two separate calibration pipe samples for the two types of cracking conditions.

It will be apparent to those skilled in the signal processing art that various approaches may be taken to implementing a crack detection instrument 60 (FIG. 1) including an algorithm tuning function 61 to perform the basic method of this invention. Generally a variety of analog and digital signal processing techniques may be employed either separately or in combination. As previously mentioned, the crack detection instrument disclosed in the above-referenced Abrams application involves a combination of analog and digital signal processing techniques utilizing an approach generally depicted in FIG. 5. For purposes of considering the basic aspects of this invention, it should be understood that the crack detection instrument 60 comprises a means (64) for measuring the values of a plurality of preselected features of the return signal waveform information (i.e. the RF IN Signal input shown in FIG. 5), means (65) for combining the measured feature values in accordance with a decision algorithm, and means (66) for registering when the algorithmically combined feature values indicate a return signal from a cracking condition, with the combining means 65 including algorithm tuning means 61 which is adapted to be adjusted while the detection instrument is receiving return signal waveform information from a preselected one of the calibration pipe samples (e.g., 10 in FIG. 1A) corresponding to the selected pipe section (e.g., 70 in FIG. 1B) to tune the decision algorithm to optimize the sensitivity and specificity of the instrument for the detection of the cracking condition.

The crack detection instrument disclosed in the above-referenced Abrams application utilizes the four preselected features of the return signal waveform as previously disclosed. The percentage power band 1 and percentage power band 2 measurements are performed by analog circuit techniques and the rise time measurement circuit 64C and duration time measurement circuit 64 are basically digital signal processing circuits. The combining-decision circuits involve both analog and digital signal processing and the indicator circuit 66 is a simple analog display function. The algorithm tuning function 61 is performed in an analog fashion utilizing weighting potentiometers. For purposes of disclosure of an exemplary specific embodiment of apparatus for carrying out the method of this invention, the complete specification of the above-referenced Abrams co-pending application is hereby specifically incorporated by reference.

It should be apparent to those skilled in the signal processing art that generally the same digital signal processing techniques which were utilized in performing the ultrasonic examination studies to arrive at the selection of return signal features and a decision algorithim for distinguishing crack and geometry signals could be utilized to carry out the two steps of the process of this invention which involve ultrasonic examination in terms of the return signal features. In other words a microcomputer or minicomputer system could be readily programmed to perform the same general feature measurement techniques as are performed by the analog/digital circuitry disclosed in the referenced Abrams co-pending application. Digital signal processing techniques involving the use of fast Fourier transform functions could be utilized to measure the percentage signal power in selected frequency bands to obtain signal feature information corresponding to that obtained in the analog circuits 64A and 64B shown in FIG. 5. The rise time and duration time measurements could readily be performed by a relatively simple counting subroutine to determine the number of digitizing time slots occupied by the rise time portion of the pulse envelope and the number of digitizing time slots occupied by the total pulse envelope, utilizing selected criteria for the initiation and termination of the rise time period and initiation and termination of the duration time period. It should thus be understood that the method of this invention is not limited in its performance to the crack detection instrument depicted schematically in FIG. 5 and disclosed in detail in the above-referenced Abrams co-pending application but can be implemented in a wide variety of special purpose or general purpose digital signal processing equipment.

Another aspect involved in this invention is the provision of a kit of apparatus for in-service ultrasonic detection of cracking conditions in pipe sections of different varieties and configurations in conjunction with an ultrasonic test instrument, such as UT instrument 40 in FIG. 1A and a trunsducer assembly such as transducer assembly 20 in FIG. 1A. The kit aspect of this invention involves the provision of a plurality of different calibration pipe samples each having prearranged configurations with inherent geometric reflectors substantially corresponding to those of one of the pipe sections which will be encountered in in-service ultrasonic measurements with each of the calibration pipe samples also having at least one known cracking condition, e.g., an IGSCC condition of either a critical or a subcritical character. FIGS. 6A, 6B, and 6C generally illustrate the concept of providing a plurality of different calibration pipe samples having different wall thicknesses and different geometric configurations. Contrasting FIGS. 6A and 6B, for example, varieties of the calibration pipe samples may involve simply differences in the wall thickness of the calibration pipe sample. It should be understood, however, that in connection with the provision of critical cracking conditions it is important that the kit include specific calibration pipe samples having precisely the critical cracking condition which is established as a standard for that particular pipe section configuration. As depicted in FIG. 6C it is also within the purview of the kit aspect of this invention to provide calibration pipe samples having a specific geometry corresponding to the geometry of the test pipe section to be encountered in a nuclear reactor piping system. Accordingly FIG. 6C shows a test at a calibration pipe sample having an elbow. The reason for providing such a calibration pipe sample in this type of configuration is again to provide for close imitation of the geometric reflectors which will be encountered in actual practice of in-service examination with the crack detection instrument.

It should be understood that the above description of specific method steps and apparatus in accordance with the principles of this invention are given by way of example only and that numerous modifications could be made therein without departing from the scope of this invention as claimed in the following claims.

What is claimed:

1. In a method of in-service ultrasonic detection of a cracking condition in a pipe section of predetermined configuration, the steps of:
   (a) selecting a plurality of ultrasonic return signal features and a tunable algorithmic combination of the measured values thereof whose resultant value is useful in distinguishing return signals from a cracking condition and from geometric reflectors, said selection being based on prior ultrasonic examination studies on a plurality of pipe samples having a variety of known geometric reflectors and known cracking conditions;
   (b) providing a calibration pipe sample having a prearranged configuration with geometric reflectors substantially corresponding to said pipe section and at least one known cracking condition;
   (c) performing an ultrasonic examination of said calibration pipe sample to measure the values of said selected return signal features while tuning said tunable algorithmic combination to optimize the capability of said algorithmic combination to distinguish return signals from said geometric reflectors and said known cracking condition;
   (d) performing an ultrasonic examination of said pipe section using the same selected return signal features and said tuned algorithmic combination of the values thereof to ascertain the presence or absence of a cracking condition therein.

2. The method of claim 1, wherein said pipe section and pipe samples are stainless steel pipe sections subject to intergranular stress corrosion cracking; said known cracking condition in said calibration pipe sample is an intergranular stress corrosion cracking condition, and said selected return signal features include selected frequency spectrum and waveform features.

3. The method of claim 2 wherein said selected frequency features include percentage signal power in each of two preselected frequency bands of the return signal frequency spectrum and said waveform features include pulse envelope rise time and duration time.

4. The method claimed in any of claims 1, 2, and 3, wherein said known cracking condition has a critical size and said algorithmic combination of said measured values of said selected return signal features is selected to enable distinguishing cracking conditions of critical size from cracking conditions of subcritical size.

5. In a kit used for in-service ultrasonic detection of cracking conditions in pipe sections of different varieties and configurations in conjunction with an ultrasonic test instrument and a transducer assembly;
   (a) a plurality of different calibration pipe samples each having a prearranged configuration with inherent geometric reflectors substantially corresponding to those of one of said pipe sections and a known cracking condition; and (b) a crack detection instrument adapted to receive output signals from said ultrasonic test instrument representing return signal waveform information from a selected pipe section under test for indicating whether said return signal is from a geometric reflector or from a cracking condition therein, said instrument comprising means for measuring the values of a plurality of preselected features of said return signal waveform information, means for combining said measured feature values in accordance with a preselected decision algorithm having tunable variables, and means for registering when said algorithmically combined feature values indicate a return signal from a cracking condition, said combining means including algorithim tuning means adapted to be adjusted while said detection instrument is receiving return signal waveform information from a preselected one of said calibration pipe samples corresponding to said selected pipe section to alter said tunable variables of said decision algorithm to optimize the sensitivity and specifically of said instrument for detection of said cracking condition said features and said decision algorithm being preselected on the basis of experimental data from prior ultrasonic examination studies on a plurality of pipe samples having a variety of known geometric reflectors and known cracking conditions such that said decision algorithm provides a high degree of discrimination between geometric reflectors and cracking conditions.

6. The kit of claim 5, wherein said known cracking condition in said calibration pipe samples are critical flaws and said algorithm tuning means is adapted to be adjusted while said detection instrument is receiving return signals from a critical flaw on a preselected one of said calibration pipe samples such that said registering means will indicate a return signal from a cracking condition equal to or greater than said critical flaw when said detection instrument is used on a selected pipe section under test.

* * * * *